(12) United States Patent
Horton et al.

(10) Patent No.: US 6,372,684 B1
(45) Date of Patent: Apr. 16, 2002

(54) CATALYST SYSTEM FOR α-OLEFIN OLIGOMERIZATION

(75) Inventors: Andrew D. Horton, Amsterdam; Bart Johan Ruisch, Hilversum; Klaas L. von Hebel, Kortenhoef; Henderikus Hyacinthus Deuling, Warmenhuizen, all of (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/292,139

(22) Filed: Apr. 15, 1999

(30) Foreign Application Priority Data

Apr. 15, 1998 (EP) ............................................. 98201193

(51) Int. Cl.[7] ................................................. B01J 31/18
(52) U.S. Cl. ................ 502/155; 502/202; 502/129; 502/128; 502/152; 502/117; 502/111; 526/126; 526/127; 526/133; 526/161; 526/943
(58) Field of Search ................. 502/155, 202, 502/129, 128, 152, 117, 111; 526/126, 127, 133, 161, 943

(56) References Cited

U.S. PATENT DOCUMENTS 5,726,115 A * 3/1998 Horton et al. ............... 502/152
5,849,653 A * 12/1998 Dall'Occo et al. ........... 502/117

FOREIGN PATENT DOCUMENTS

| WO | WO 92/12162 | 7/1992 |
| WO | WO 94/25416 | 11/1994 |
| WO | WO 96/02580 A1 | 2/1996 |
| WO | WO 96/27439 | 9/1996 |
| WO | WO 96/21899 | 5/1999 |

* cited by examiner

*Primary Examiner*—David W. Wu
*Assistant Examiner*—Ling-Siu Choi

(57) ABSTRACT

It is disclosed a new catalyst system, having high catalytic activity in the oligomerization of α-olefins, comprising a bridged bis-amido Group 4 metal compound of formula (I):

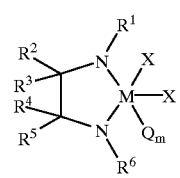

(I)

wherein M is Ti, Zr or Hf; Y is Si, Ge or Sn; X is a hydrogen, halogen or an hydrocarbon radical; $R^1$, $R^2$, $R^3$, $R^4$, $R^5$ and $R^6$ are hydrocarbon radicals, optionally containing Si, Ge, O, S, P, B or N atoms; Q is a neutral Lewis base; and m is 0–2; in association with a boron activating compound, and with one or more branched alkylaluminiums and/or alumoxanes of branched alkylaluminiums; said catalyst system allows oligomers to be obtained in high yields, with a high selectivity towards α-oligomers.

42 Claims, No Drawings

CATALYST SYSTEM FOR α-OLEFIN OLIGOMERIZATION

FIELD OF THE INVENTION

The present invention relates to new catalyst systems and to their use in the oligomerization and co-oligomerization of (α-olefins; said catalyst systems are particularly useful in ethylene oligomerization in order to obtain α-olefinic oligomers having from 4 to 24 carbon atoms.

PRIOR ART DISCLOSURE

High linear α-olefins, i.e. (α-olefins having from 4 to 24 carbon atoms, and more specifically 6 to 20 carbon atoms, are in great demand as intermediates in the preparation of detergents, lubricant additives and polyolefins; α-olefins having 6–20 carbon atoms are suitable for a large number of applications in different technical fields. However, oligomerization processes commonly known in the state of the art lead to the obtainment, together with the target products, of undesirable by-products, such as internal olefins, branched olefins and olefins having a number of carbon atoms outside the above mentioned range.

Olefin polymerization processes employing homogeneous Ziegler-Natta catalyst systems or metallocene/alumoxane catalyst systems are well known in the state of the art; these catalyst systems are also used in oligomerization processes of lower olefins to give higher olefins.

For instance, the British patent application GB 135,873 describes the preparation of $C_4$–$C_{20}$ linear α-olefins by ethylene oligomerization in the presence of a catalyst composition comprising a divalent nickel salt, a boron hydride and a tertiary organophosphorus compound.

The international patent application WO 94/25416 discloses a catalyst system for the preparation of $C_4$–$C_{24}$ linear α-olefins comprising the reaction product of a bis-tetramethyl-cyclopentadienyl metallocene and a bulky, labile and non-coordinating anion.

Bridged bis-amido Group 4 (IUPAC 1988 notation) metal compounds are also known, as components of catalyst systems for the preparation of polyolefins, such as polyethylene and polypropylene. The international patent application WO 92/12162 discloses catalyst systems for the polymerization of α-olefins, comprising an amido transition metal compound having the following formula:

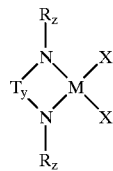

wherein M is Ti, Zr or Hf; X is an univalent anionic ligand; the groups R, linked to trivalent N atoms, are selected from halogens and linear or branched hydrocarbon radicals, optionally containing one or more heteroatoms; T is a covalent unsubstituted or substituted hydrocarbon bridging group, optionally containing one element of Group IV-A or VI-A (Deming notation; corresponding to Group 14 and 16 of the IUPAC 1988 notation); y is 1 or 0; z is 2-y; in association with an alumoxane.

Suitable alumoxanes are obtained by hydrolysis of a trialkylaluminium or haloalkylaluminium, such as trimethylaluminium, triethylaluminium and the corresponding chlorides; the most preferred alumoxane is methylalumoxane (MAO).

The catalysts disclosed in the above-mentioned WO 92/12162, which do not envisage amido compounds having a bridging group containing two heteroatoms, are used in the production of high molecular weight polyolefins, having a molecular weight well in excess of 100,000, and more specifically of high molecular weight isotactic polypropylene.

The international patent application WO 96/27439 describes a new class of oligomerization catalysts comprising a bridged bis-amido Group 4 metal compound, such as {1,2-bis(t-butylamide)tetramethyl-disilane{-zirconium dibenzyl or dimethyl, in association with suitable activating agents, capable of providing a bulky, labile and non-coordinating anion, containing at least one boron atom, such as $B(C_6F_5)_3$ or $[Me_2PhNH]^+[B(C_6F_5)_4]^-$.

These catalyst systems are active in the oligomerization or co-oligomerization of α-olefins to produce linear α-olefins. In the specification of WO 96/27439 it is mentioned the possibility of adding to the catalytic compositions further components, for example in order to increase the solubility and/or the stability of the same compositions, although not affecting the catalytic activity. For instance, it is mentioned the possibility of adding organoaluminium compounds, such as trimethylaluminium (TMA), triethylaluminium (TEA), triisopropylaluminium and triisobutylaluminium (TIBA), acting as scavenging agents, although without any influence of the catalytic activity of the system.

Nevertheless, there is room for improvement in the oligomerization yields when these catalyst systems are used. They tend to be sensitive to the presence of minor contaminants, resulting in low yields. In order to achieve a satisfactory activity the catalyst concentrations should not be too low, whereas relatively high concentrations may lead to exothermic reactions which are difficult to control. Further, the activity stability of the catalyst systems described in WO 96/27439 is not optimal, as shown by their activity decay.

Therefore, it is felt the need of lowering the decay rate and improving the catalytic activity of the above mentioned oligomerization catalysts, in order to allow their industrial exploitation.

SUMMARY OF THE INVENTION

The Applicant has now unexpectedly found that the catalytic activity in α-olefin oligomerization of the above-mentioned bridged bis-amido Group 4 metal compounds, in association with boron activating compounds, can be surprisingly enhanced by adding to these components a specific class of branched alkylaluminiums and/or alumoxanes of branched alkylaluminiums, leading to α-olefin oligomers having from 4 to 30 carbon atoms, in high yields and with a high selectivity towards α-olefins.

More specifically, the present invention concerns a catalyst system for α-olefin oligomerization comprising the product obtainable by contacting the following components:

(A) one or more bis-amido compounds having formula (I):

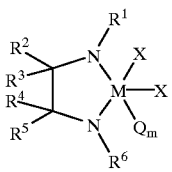

(I)

wherein M is Ti, Zr or Hf;

N is a trivalent nitrogen atom;

the Y atoms, the same or different from each other, are selected from the group consisting of Si, Ge and Sn;

the X groups, the same or different from each other, are selected from the group consisting of H, halogen, linear or branched, saturated or unsaturated $C_1$–$C_{20}$ alkyl, $C_1$–$C_{20}$ alkoxyl, $C_3$–$C_{20}$ cycloalkyl, $C_6$–$C_{20}$ aryl, $C_6$–$C_{20}$ aryloxyl, $C_7$–$C_{20}$ alkylaryl and $C_7$–$C_{20}$ arylalkyl radicals, optionally containing one or more Si, Ge, O, S, P, B or N atoms; or two X groups form a ring having from 4 to 8 members;

$R^1$, $R^2$, $R^3$, $R^4$, $R^5$ and $R^6$, the same or different from each other, are linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radicals, optionally containing one or more Si, Ge, O, S, P, B or N atoms; or are $Si(R^7)_3$ groups, wherein the groups $R^7$, the same or different from each other, are linear or branched, saturated or unsaturated $C_1$–$C_{10}$ alkyl, $C_3$–$C_{10}$ cycloalkyl, $C_6$–$C_{15}$ aryl, $C_7$–$C_{15}$ alkylaryl or $C_7$–$C_{15}$ arylalkyl groups; or two or four substituents of $R^1$, $R^2$, $R^3$, $R^4$, $R^5$ and $R^6$, linked to two vicinal atoms, form one or two rings having from 4 to 8 members;

Q is a neutral Lewis base; and m is an integer ranging from 0 to 2;

said bis-amido compound being optionally present in the form of a dimer;

(B) one or more activating cocatalysts selected from:
compounds having formula $Y^+Z^-$, wherein $Y^+$ is a cation capable of reacting irreversibly with a substituent X of the compound of formula (I), and Z– is a compatible non-coordinating anion comprising at least one boron atom; and neutral strongly Lewis acidic compounds comprising at least one boron atom;

(C) one or more compounds selected from the following classes:
(a) organometallic aluminium compounds having formula (II):

$$Al(CH_2—CR^8R^9R^{10})_x R^{11}{}_y H_z \quad \text{(II)}$$

wherein, in the ($CH_2$—$CR^8R^9R^{10}$) groups, the same or different from each other, $R^8$ is a linear or branched, saturated or unsaturated $C_1$–$C_{10}$ alkyl, $C_3$–$C_{13}$ cycloalkyl or $C_7$–$C_{16}$ alkylaryl radical; $R^9$ is a saturated or unsaturated $C_1$–$C_{50}$ alkyl, $C_3$–$C_{50}$ cycloalkyl, $C_6$–$C_{50}$ aryl, $C_7$–$C_{50}$, alkylaryl or $C_7$–$C_{50}$ arylalkyl radical, said radical being different from a straight alkyl or alkenyl group; or $R^8$ and $R^9$ form together a ring having from 4 to 6 carbon atoms; $R^{10}$ is hydrogen or a linear or branched, saturated or unsaturated $C_1$–$C_{10}$ alkyl, $C_6$–$C_{15}$ aryl, $C_7$–$C_{16}$ alkylaryl radical or arylalkyl radical, optionally containing one or more Si or Ge atoms;

$R^{11}$ is a linear or branched, saturated or unsaturated $C_1$–$C_{10}$ alkyl, $C_3$–$C_{15}$ cycloalkyl, $C_6$–$C_{15}$ aryl, $C_7$–$C_{16}$ alkylaryl or $C_7$–$C_{16}$ arylalkyl radical;

x is an integer ranging from 1 to 3; z is 0 or 1; and y is 3-x-z; and (b) the reaction products of water with organometallic aluminium compounds of formula (III):

$$AlR^{12}{}_{3-w}H_w \quad \text{(III)}$$

wherein the substituents $R^{12}$, the same or different from each other, are selected from the group consisting of linear or branched, saturated or unsaturated $C_1$–$C_{50}$ alkyl, $C_3$–$C_{50}$ cycloalkyl, $C_6$–$C_{50}$ aryl, $C_7$–$C_{50}$ alkylaryl and $C_7$–$C_{50}$ arylalkyl radicals, optionally containing one or more Si or Ge atoms, wherein at least one of said substituents $R^{12}$ is different from a straight alkyl group; and w is 0 or 1; the molar ratio between said organometallic aluminium compound and water being comprised between 1:1 and 100:1.

The present invention further provides a process for the oligomerization of olefins comprising the reaction of oligomerization of one or more olefinic monomers in the presence of a catalyst system as reported above.

DETAILED DESCRIPTION OF THE INVENTION

The catalyst systems for olefin oligomerization and the process using them, according to the present invention, will be better described in the following detailed description.

In the bis-amido compounds (A) having formula (I), M is Ti, Zr or Hf, and preferably is Zr. The groups Y are preferably the same, and are more preferably two Si atoms.

The groups X are preferably selected from hydrogen, methyl, ethyl, propyl, n-butyl, phenyl, 4-alkyl-phenyl and benzyl groups; two X groups can form, together with the metal M, a ring having from 4 to 8 members, and preferably a metallacyclobutane.

$R^1$, $R^2$, $R^3$, $R^4$, $R^5$ and $R^6$, the same or different from each other, are preferably methyl, ethyl, propyl, n-butyl, t-butyl, t-amyl, cyclohexyl, phenyl, dimethyl-phenyl, diisopropyl-phenyl, trimethylsilyl, tri-t-butyl-silyl, phenylmethyl-ethyl, diphenyl-ethyl and triphenyl-methyl.

Preferred examples of the neutral Lewis base Q are diethylether, tetrahydrofuran, dimethylaniline, aniline, n-butylamine and trimethylphosphine.

Preferred bis-amido compounds of formula (I) according to the present invention are:

{1,2-bis(t-butylamide)-tetramethyldisilane}metal dibenzyl {$(Me_2SiNCMe_3)_2$}$M(CH_2Ph)_2$ {1,2-bis(t-butylamide)-tetramethyldisilane}metal dimethyl, {$(Me_2SiNCMe_3)_2$}$MMe_2$ {1,2-bis(t-butylamide)-tetramethyldisilane}metal di(n-butyl), {$(Me_2SiNCMe_3)_2$}$M(n-Bu)_2$ {1,2-bis(t-butylamide)-tetramethyldisilane}metal diphenyl, {$(Me_2SiNCMe_3)_2$}$MPh_2$ {1,2-bis(t-butylamide)-tetramethyldisilane}metal di(4-methylphenyl), {$(Me_2SiNCMe_3)_2$}$M$ {$CH_2(4\text{-Me-Ph})$}$_2$ {1,2-bis(t-butylamide)-tetramethyldisilane}metallacyclobutane, {$(Me_2SiNCMe_3)_2$}{$MCH_2CH_2CH_2$}

{1,2-bis(t-butylamide)-tetramethyldisilane}metal dihydride, {$(Me_2SiNCMe_3)_2$}$MH_2$ {1,2-bis(t-amylamide)-tetramethyldisilane}metal dibenzyl, {$(Me_2SiNCMe_2Et)_2$}$M(CH_2Ph)_2$ {1,2-bis(cyclohexylamide)-tetramethyldisilane}metal dibenzyl, {$(Me_2SiNCy)_2$}$M(CH_2Ph)_2$ {1,2-bis(ethylamide)-tetramethyldisilane}metal dibenzyl, {$(Me_2SiNEt)_2$}$M(CH_2Ph)_2$ {1,2-bis(phenylamide)-tetramethyldisilane}metal
dibenzyl, {(Me$_2$SiNPh)$_2$}M(CH$_2$Ph)$_2$ {1,2-bis(2,6-dimethylphenylamide)-
tetramethyldisilane}metal dibenzyl, {(Me$_2$SiN[2,6-
Me$_2$-Ph])$_2$}M(CH$_2$Ph)$_2$ {1,2-bis(trimethylsilylamide)-tetramethyldisilane}metal
dibenzyl, {(Me$_2$SiNSiMe$_3$)$_2$}M(CH$_2$Ph)$_2$ {1,2-bis{tri(t-butyl)silylamide)-
tetramethyldisilane}metal dibenzyl, [{(Me$_2$SiNSi(CMe$_3$)$_3$}$_2$]M(CH$_2$Ph)$_2$ {1,2-bis(t-butylamide)-tetraethyldisilane}metal dibenzyl,
{(Et$_2$SiNCMe$_3$)$_2$}M(CH$_2$Ph)$_2$ {1,2-bis(t-butylamide)-tetraethyldisilane}metal dimethyl,
{(Et$_2$SiNCMe$_3$)$_2$}MMe$_2$ {1,2-bis(t-butylamide)-tetraphenyldisilane}metal
dibenzyl, {(Ph$_2$SiNCMe$_3$)$_2$}M(CH$_2$Ph)$_2$ {1,2-bis(t-butylamide)-tetramethyldigermane}metal
dibenzyl, {(Me$_2$GeNCMe$_3$)$_2$}M(CH$_2$Ph)$_2$ {1,2-bis(t-butylamide)-tetramethyldistannane}metal
dibenzyl, {(Me$_2$SnNCMe$_3$)$_2$}M(CH$_2$ph)$_2$, {1,2-bis(1,1,3,3-tetramethylbutylamide)-
tetramethyldisilane}metal dibenzyl,
{(Me$_2$SiNCMe$_2$CH$_2$CMe$_3$)$_2$}M(CH$_2$Ph)$_2$, and {1,2-bis(2,6-diisopropylphenylamide)-
tetramethyldisilane}metal dibenzyl, {(Me$_2$SiN[2,6-
iPr$_2$Ph])$_2$}M(CH$_2$Ph)$_2$, wherein M has the meaning reported above.

The bis-amido Group 4 metal compounds of formula (I), i.e. components (A) of the catalyst systems of the invention, can be prepared according to procedures known in the state of the art, and more specifically as described in the international patent application WO 96/27439. Said bis-amido compounds can be in the form of a dimer, corresponding to the following formula (IV):

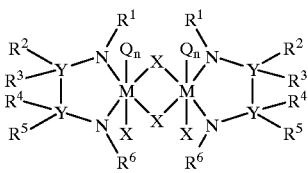

(IV)

wherein M, Y, X, R$^1$, R$^2$, R$^3$, R$^4$, R$^5$, R$^6$ and Q have the meaning reported above and n is 0 or 1.

The catalyst systems of the invention further comprise one or more activating cocatalysts (component B) of formula Y$^+$Z$^-$, wherein Y$^+$ is a cation capable of reacting irreversibly with a substituent X of the compound of formula (I) or (IV), and Z$^-$ is a bulky and labile anion, substantially non-coordinating under the reaction conditions, and containing at least one boron atom. Further suitable activating cocatalysts are neutral Lewis acidic compounds, containing at least one boron atom, which are capable of abstracting one of the radicals X of the first component, thereby also contributing an anion Z$^-$. Said anion must be capable of stabilizing the active catalytic species originating by the reaction of the compound (I) or (IV) with said activating cocatalyst and must be sufficiently labile to be able to be displaced by an olefinic substrate.

Components (A) and (B) form together an ionic compound of formula (V):

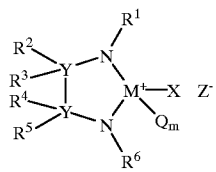

(V)

wherein M, Y, X, R$^1$, R$^2$, R$^3$, R$^4$, R$^5$, R$^6$, Q, Z and m have the meaning reported above; or, when the component (A) is in the form of the above reported dimer (IV), an ionic compound of formula (VI):

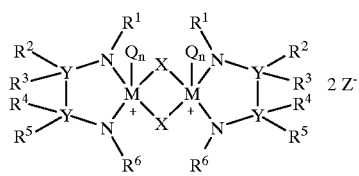

(VI)

wherein M, Y, X, R$^1$, R$^2$, R$^3$, R$^4$, R$^5$, R6, Q, Z and n have the meaning reported above. In component (B), Y$^+$ is preferably a Broensted acid, capable of donating a proton and of reacting irreversibly with a substituent X of the compound of formula (I) or (IV); the cation Y$^+$ is preferably a quaternary ammonium cation, and more preferably a trihydrocarbyl-ammonium cation, such as tri-n-butylammonium and dimethylanilinium.

Alternatively Y$^+$ is a not proton-donating cation, in particular a metal cation, such as a silver ion or a triphenyl carbenium ion.

In component (B), the anion Z$^-$, containing one boron atom, is preferably a borate of formula [B(R')$_4$]$^-$, wherein R$^1$ is selected from the group consisting of hydrogen, C$_1$–C$_{10}$ alkyl, C$_3$–C$_{10}$ cycloalkyl, C$_6$–C$_{15}$ aryl, C$_7$–C$_{15}$ alkylaryl and C$_7$–C$_{15}$ arylalkyl groups, optionally substituted with one or more halogens; suitable examples are [B(C$_6$F$_5$)$_4$]$^-$, [R'B(C$_6$F$_5$)$_3$]$^-$, [B(FC$_6$H$_4$)$_4$]$^-$, [R'B(FC$_6$H$_4$)$_3$]$^-$, [B{(CF$_3$)$_2$(C$_6$H$_3$)}$_4$]$^-$ and [R'B{(CF$_3$)$_2$(C$_6$H$_3$)}$_3$]$^-$, wherein R' has the meaning reported above. Examples of anion Z$^-$ containing a plurality of boron atoms are the carborates, such as [B$_{11}$CH$_{12}$]$^-$.

The activating cocatalyst Y$^+$Z$^-$ is preferably selected from the group consisting of:

dimethylanilinium tetrakis(pentafluorophenyl)borate [PhMe$_2$NH][B(C$_6$F$_5$)$_4$], tri(n-butyl)ammonium tetrakis(pentafluorophenyl)borate [Bu$_3$NH][B(C$_6$F$_5$)$_4$], dimethylanilinium tetrakis(2,3,5,6-tetrafluorophenyl) borate [PhMe$_2$NH][B(2,3,5,6—C$_6$F$_4$H)$_4$], dimethylanilinium tetrakis(3,5-bis-trifluoromethyl-phenyl)borate [PhMe$_2$NH][B(3,5-(CF$_3$)$_2$—C$_6$H$_3$)$_4$], dimethylanilinium tetrakis(4-fluorophenyl)borate [PhMe$_2$NH][B(4-C$_6$H$_4$F)$_4$], dimethylanilinium tetraphenylborate [PhMe$_2$NH][B(C$_6$H$_5$)$_4$], triphenylcarbonium tetrakis(pentafluorophenyl)borate [Ph$_3$C][B(C$_6$F$_5$)$_4$], ferrocenium tetrakis(pentafluorophenyl)borate [(C$_5$H$_5$)$_2$Fe][B(C$_6$F$_5$)$_4$], silver tetrakis(pentafluorophenyl)borate [Ag][B(C$_6$F$_5$)$_4$], tri(n-butyl)ammonium 1-carbodecaborate [Bu$_3$NH][CB$_{11}$H$_{12}$] and diethyloxonium tetrakis(3,5-bis-trifluoromethyl-phenyl) borate [H(OEt$_2$)$_2$][B(3,5-(CF$_3$)$_2$—C$_6$H$_3$)$_4$].

When component (B) is a neutral strongly Lewis acidic compound, it is preferably selected from the group consisting of:

tris(pentafluorophenyl)borane B(C$_6$F$_5$)$_3$, tris(2,3,5,6-tetrafluorophenyl)borane B(2,3,5,6-C$_6$F$_4$H)$_3$, and trimethylboron B(CH$_3$)$_3$.

The boron containing components (B) of the catalyst systems of the invention can be prepared according to procedures known in the state of the art, and in particular as described in the international patent application WO 96/27439.

Component (C) of the catalyst systems according to the present invention can be one or more organometallic aluminium compounds belonging to the following classes:

(a) organometallic aluminium compounds of formula (II):

wherein R$^8$, R$^9$, R$^{10}$, R$^{11}$, x, y and z have the meaning reported above; and (b) reaction products of water with organometallic aluminium compounds of formula (III)

wherein R$^{12}$ and w have the meaning reported above.

In the organometallic aluminium compound belongs to the class (a), formula (II), R$^8$ is preferably methyl or ethyl; R$^9$ is preferably a saturated or unsaturated branched-chain C$_3$–C$_{30}$ alkyl or alkylaryl group, and more preferably a C$_4$–C$_{10}$ alkyl or alkylaryl group, or it is an optionally substituted phenyl group; R$^{10}$ is preferably hydrogen; R$^{11}$ is preferably a C$_1$–C$_5$ alkyl group, and more preferably an isobutyl group.

The above organometallic aluminium compounds can be suitably prepared according to the methods known in the state of the art, and preferably as described in the international patent application WO 96/02580.

A subclass of organometallic aluminium compounds particularly advantageous in the catalyst systems according to the present invention are the compounds of formula (II) wherein the (CH$_2$—CR$^8$R$^9$R$^{10}$) groups, the same or different from each other, are β,δ-branched groups, corresponding to formula (CH$_2$—CR$^8$R$^{10}$—CH$_2$—CR$^{13}$R$^{14}$R$^{15}$), wherein R$^8$ and R$^{10}$ have the meaning reported above; R$^{13}$ and R$^{14}$, the same or different from each other, are linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl radicals; and R$^{15}$ is hydrogen or has the same meaning of R$^{13}$ and R$^{14}$. Non limiting examples of these compounds are tris(2,4,4-trimethylpentyl)aluminium (TIOA), bis(2,4,4-trimethylpentyl)aluminium hydride, isobutyl-bis(2,4,4-trimethylpentyl)aluminium, diisobutyl-(2,4,4-trimethylpentyl)aluminium, tris(2,4-dimethylheptyl)aluminium and bis(2,4-dimethylheptyl)aluminium hydride.

Another particular class of organometallic aluminium compounds of formula (II), suitable as a component (C) of the catalyst systems of the invention, are those wherein the (CH$_2$—CR$^8$R$^9$R$^{10}$) groups derive from the product of the oligomerization of lower α-olefins, such as propylene or 1-butene. In this case, x is preferably 1 or 2.

These compounds can be prepared as described in the above-mentioned international patent application WO 96/02580.

A particularly preferred subclass of organometallic aluminium compounds is constituted by the compounds of formula (II) wherein the (CH$_2$—CR$^8$R$^9$R$^{10}$) groups, the same or different from each other, are β,γ-branched groups, corresponding to formula (CH$_2$—CR$^8$R$^{10}$—CR$^{13}$R$^{14}$R$^{15}$), wherein R$^8$, R$^{10}$, R$^{13}$, R$^{14}$ and R$^{15}$ have the meaning reported above. In said subclass, R$^8$ is preferably a C$_1$–C$_5$, more preferably a C$_1$–C$_3$ alkyl group; according to a preferred embodiment, said R$^8$ is methyl. R$^{10}$ is preferably hydrogen. R$^{13}$ and R$^{14}$ are preferably C$_1$–C$_5$, and more preferably C$_1$–C$_3$ alkyl groups. R$^{15}$ is preferably hydrogen or a C$_1$–C$_5$ alkyl group, and more preferably a C$_1$–C$_3$ alkyl group.

Within this subclass, particularly preferred organometallic aluminium compounds are: tris(2,3-dimethyl-butyl)aluminium, tris(2,3,3-trimethyl-butyl)aluminium, tris(2,3-dimethyl-pentyl)aluminium, tris(2,3-dimethyl-hexyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, and the corresponding compounds wherein one of the hydrocarbyl groups is replaced by hydrogen, and those wherein one or two of the hydrocarbyl groups are replaced by an isobutyl group.

These organoaluminium compounds can be prepared according to procedures known in the state of the art, and in particular as described in the International Application no. PCT/EP 98/06732.

When component (C) of the catalyst systems according to the present invention belongs to class (b), it is the reaction product of water with an organometallic aluminium compounds of formula (III), as reported above. The molar ratio between said organometallic aluminium compound and water ranges from 1:1 to 100:1, and preferably from 1:1 to 50:1. A particularly advantageous value of said molar ratio is 2:1.

In formula (III), R$^{12}$ is preferably a substituted or unsubstituted non-straight C$_1$–C$_{10}$ alkyl or C$_7$–C$_{16}$ alkylaryl, optionally containing Si or Ge atoms; more preferably, all the substituents R$^{12}$ are isoalkyl radicals.

The compounds of formula (III) are preferably selected from the group consisting of Al(iBu)$_3$ (TIBA), AlH(iBu)$_2$, Al(iHex)$_3$, Al(C$_6$H$_5$)$_3$, Al(CH$_2$C$_6$H$_5$)$_3$, Al(CH$_2$CMe$_3$)$_3$, Al(CH$_2$SiMe$_3$)$_3$, AlMe$_2$iBu and AlMe(iBu)$_2$.

According to a further preferred embodiment of the catalyst system of the invention, said organometallic aluminium compounds of formula (III) corresponds to the compounds of formula (II), as reported above, and the preferred compounds are the above-mentioned ones.

According to a further preferred embodiment of the invention, in said compound of formula (III), at least one R$^{12}$ group has formula (CH$_2$—CR$^8$R$^9$R$^{10}$), wherein R$^8$, R$^9$ and R$^{10}$ have the meaning reported above; more preferably said R$^{12}$ group is a β,δ-branched or a β,γ-branched group.

When component (C) belong to class (b), water can be gradually added to the alkyl aluminium compound of formula (III) in solution, in an aliphatic or aromatic inert hydrocarbon solvent such as heptane or toluene; preferably, compound (C) of formula (III) can be brought into contact with the wet monomer or solvent in the reactor and the mixture of components (A) and (B) and an additional amount of compound (C) is then introduced into the reactor.

According to another embodiment, water can be reacted in combined form as hydrated salt, or it can be absorbed or adsorbed on an inert support, such as silica. According to a further embodiment, the alkyl aluminium compound (III) can be allowed to react with boric anhydride or with boric acid.

The components of the catalyst system according to the present invention can be brought into contact in different manners. The catalyst system may be formed by mixing together components (A), (B) and (C), following different orders of addition, preferably in solution, in a suitable non-polar solvent such as toluene, benzene, chlorobenzene, an alkane or an alkene, to form a liquid catalyst system. A preferred way of forming the catalyst system of the invention comprises first mixing components (A) and (B), and subsequently adding to the obtained mixture a solution of component (C), preferably in toluene.

The three-components catalyst system may be formed prior to its introduction into the reaction vessel, or it may be formed in situ.

Components (A) and (B) are preferably employed with a molar ratio ranging from 0.1:1 to 5:1, and more preferably ranging from 0.9:1 to 1.1:1.

The molar ratio between the aluminium of component (C) and the metal M of the bis-amido compound (A) preferably ranges from 1:1 to 1000:1, more preferably from 10.1 to 500:1, and even more preferably from 20:1 to 150:1.

The catalysts of the present invention can also be used on inert supports. This is achieved by depositing the components (A), (B) and/or (C), either singly or in mixture, on inert supports such as silica, alumina, silica/alumina, titania, zirconia, magnesia; suitable inert supports are olefin polymers or prepolymers, such as polyethylenes, polypropylenes or styrene/divinylbenzene copolymers. The thus obtained supported catalyst systems can be advantageously used in gas-phase oligomerization.

The catalyst systems according to the present invention can be conveniently used in oligomerization processes. In fact, the Applicant has surprisingly found that the presence of the component (C) in the catalyst system according to the present invention leads to higher oligomerization yields, lower decay rates and better reproducibility, as well as to a better specificity in the obtainment of α-olefins, thus avoiding the undesired formation of internal or branched olefins. Therefore, it is another object of the present invention a process for the oligomerization or co-oligomerization of a-olefins of formula $CH_2=CHR$, wherein R is hydrogen or a $C_1-C_{20}$ alkyl, $C_5-C_{20}$ cycloalkyl or $C_6-C_{20}$ aryl radical, and preferably ethylene, in order to obtain linear α-olefinic oligomers having a chain length from 4 to 30 carbon atoms and preferably 6–20 carbon atoms; said process is characterized in that the oligomerization reaction is performed in the presence of a catalyst system according to the present invention.

Non limiting examples of olefinic monomers which are suitable to be used in the oligomerization process according to the present invention are ethylene, propylene, 1-butene, 1-pentene, 1-hexene, 4-methyl-1-pentene, 4,6-dimethyl-1-heptene, 1-octene, 1-decene, 1-dodecene, 1-tetradecene, 1-hexadecene, 1-octadecene and allylcyclohexane, as well as cycloolefins (such as cyclopentene and cyclohexene) and conjugated or non-conjugated dienes (such as 1,4-hexadiene, isoprene, 1,3-butadiene, 1,5-hexadiene and 1,6-heptadienes).

The (co)oligomerization process according to the present invention can be carried out in the liquid phase or in gas phase; in the former case, it is advantageously carried out in the presence of an inert hydrocarbon solvent either aromatic, preferably toluene, or aliphatic, such as propane, hexane, heptane, isobutane, isopentane, cyclohexane and isooctane, and preferably isopentane or isooctane. Said solvent can serve even as a suitable solvent for the catalyst system.

Alternatively, the (co)oligomerization process may be carried out in an olefin solvent, and particularly in a mixture of linear α-olefins and/or higher branched or internal olefins.

The starting α-olefins can be supplied to the reactor together with an inert diluent, such as nitrogen or helium, when the reactant is gaseous, or in a liquid solvent when the reactant is in the liquid form.

The (co)oligomerization temperature is preferably comprised between −20° C. and 150° C., more preferably between 10° C. and 100° C., and even more preferably between 40 and 90° C.

The (co)oligomerization pressure is preferably comprised between 100 and 10,000 kPa, more preferably between 200 and 8,000 kPa, and even more preferably between 500 and 2,000 kPa.

Reaction times of from 1 minute to 5 hours have been found to be suitable, depending on the activity of the catalyst system and on the reaction conditions. At the end of the oligomerization reaction, a conventional catalyst deactivating agent, such as water, methanol, or another alcohol, may be added to the reaction mixture, in order to terminate the reaction The reaction can be terminated also by introducing air.

Suitable operating conditions, in particular pressure and temperature, can be selected in order to yield oligomers having a "K factor" ranging from 0.3 to 0.8, wherein said "K factor" is the molar ratio $[C_{n+2}]/[C_n]$, calculated from the slope of the graph of log $[C_n\text{mol }\%]$ versus n, wherein n is the number of carbon atoms in the olefinic product. The "K factor" gives an indication of the relative proportions of the olefins obtained from the oligomerization process.

The oligomerization product is a mixture of α-olefins, preferably linear, having a chain length ranging from 4 to 30 carbon atoms, and preferably from 6 to 20 carbon atoms. Said olefins can be suitably recovered by conventional distillation and separation techniques, known in the state of the art. It is also possible to recover unconverted starting material and/or oligomeric products having a molecular weight outside the desired molecular weight, in order to process or recycle them.

The following experimental examples are reported for illustrative and non limiting purposes.

GENERAL PROCEDURES AND CHARACTERIZATIONS

All the operations with the catalyst systems and the catalyst components (A)–(C) were carried out under nitrogen atmosphere.

Oligomerization Solvents

Isooctane (2,4,4-trimethylpentane, 99.8% purity) was dried by prolonged nitrogen purge, followed by passage over molecular sieves (water content of about 1 ppm).

Anhydrous toluene (99.8% purity) from Aldrich was dried over 4 Å molecular sieves (water content of about 3 ppm).

Ethylene (99.5% purity) was purified over a column containing 4 Å molecular sieves and BTS catalyst (purchased from BASF) in order to reduce water and oxygen content to <1 ppm.

Oligomers Characterization

In order to evaluate oligomer product distribution, oligomers were characterized by GC characterization by using a HP 5890 apparatus, with the following chromatographic conditions:

Column: Cp-Sil 5 CB, film thickness=0.4 µm, internal diameter=0.22 mm, length 50 m (by Chrompack, catalogue no. 7719, 1986); injection temperature: 340° C.; detection temperature: 340° C.; initial temperature: 35° C. for 10 minutes; temperature program rate: 10.0° C./minute; final temperature: 325° C. for 20 minutes; internal standard: n-hexylbenzene. Response factors for the even linear α-olefins and for cis- and trans-2-hexene, 2-ethyl-1-butene and n-hexylbenzene (internal standard) were determined using a standard calibration mixture. The yields of the $C_4$–$C_{30}$ olefins obtained from the GC analysis were used to calculate the "K factor" in oligomerization (via regression analysis).

The relative amounts of the different hexene isomers found from the GC analysis are a measure of the catalysts selectivity towards linear α-olefin formation.

CATALYST COMPONENTS

Component (A):
{1,2-bis(t-butylamide)tetramethyldisilane}-zirconium Dibenzyl

{1,2-bis(t-butylamide)tetramethyldisilane}-zirconium dibenzyl was prepared as described in the international patent application WO 96/27439 (Example 1.2.1).

Component (B):
[Me$_2$PhNH]$^+$[B(C$_6$F$_5$)$_4$]$^-$

Dimethylanilinium tetrakis(pentafluorophenyl)borate, [Me$_2$PhNH]$^+$[B(C$_6$F$_5$)$_4$]$^-$, was obtained from Akzo-Nobel (catalogue 1997)

Component (C):
Tris(2-methyl-propyl)aluminium (TIBA)

Tris(2-methyl-propyl)aluminium was obtained from Aldrich (catalogue n. 25, 720-6, 1996-7).

Tris(2,4,4-trimethyl-pentyl)aluminium (TIOA)

Tris(2,4,4-trimethyl-pentyl)aluminium was prepared as described in WO 96/02580.

Tris(2,3-dimethyl-hexyl)aluminium (TDMHA)

Tris(2,3-dimethyl-hexyl)aluminium was prepared as described in the International Application no. PCT/EP 98/06732.

Tris(2,3-dimethyl-butyl)aluminium (TDMBA)

Tries(2,3-dimethyl-butyl)aluminium was prepared as described in the International Application no. PCT/EP 98/06732.

(2-Methyl-propyl)aluminoxane (TIBAO)

TIBAO was either obtained from Witco as a 30% w/w solution in cyclohexane (Examples 14–17) or prepared immediately prior to use by reacting a 0.45 M toluene solution of TIBA (obtained as reported above) with a half-equivalent of water, whilst maintaining the reaction temperature in the range 5–15° C. (Example 9). In Example 3, TIBAO was prepared in situ by addition of TIBA to the autoclave containing wet isooctane (0.19 mmol water in 190 g isooctane) at 50° C. and stirring for 30 minutes.

(2,4,4-Trimethyl-pentyl)aluminoxane (TIOAO)

(2,4,4-Trimethyl-pentyl)aluminoxane was prepared immediately prior to use by reacting a 0.45 M toluene solution of tris(2,4,4-trimethyl-pentyl)aluminium (TIOA, prepared as described above) with a half-equivalent of water, whilst maintaining the reaction temperature in the range 5–15° C.

2,3-Dimethyl-hexyl)aluminoxane (TDMHAO)

(2,3-Dimethyl-hexyl)aluminoxane was prepared immediately prior to use, according to the procedure used to prepare TIOAO.

(2,3-Dimethyl-butyl)aluminoxane (TDMBAO)

(2,3-Dimethyl-butyl)aluminoxane was prepared immediately prior to use, according to the procedure used to prepare TIOAO.

Methylalumoxane (MAO)

Methylalumoxane was obtained from Akzo-Nobel as a solution in toluene (11.3% w/w Al, 1997).

CATALYST SYSTEM PREPARATION

Catalyst preparation was carried out under nitrogen in a Braun MB 200-G dry box. Component (A) and Component (B) were placed in a reaction bottle. A mixture of toluene and component (C) was added to the stirred mixture, which was then maintained under stirring for 20 minutes, giving a very pale yellow homogeneous solution. This solution was then used immediately in the oligomerization reaction.

OLIGOMERIZATION TRIALS

COMPARATIVE EXAMPLES 1, 2, 4, 8 and 13, and EXAMPLES 3, 5–7, 9–12 and 14–17.

Oligomerization trials were performed in a 1-litre steel autoclave, with jacket cooling with two Julabo baths, with anchor stirrer (autoclave 1) or turbine/gas stirrer (autoclave 2). In order to remove traces of water from the reactor, the reactor was evacuated overnight at 2 kPa, at 70° C. The reactor temperature was then decreased to 50° C. and the reactor pressurized with $N_2$ (100 kPa). Subsequently, the reactor was scavenged with a solution of TIBA (100 mg in Autoclave 1, Examples 1–12; 300 mg in Autoclave 2, Example 13) or TIBAO (300 mg in Autoclave 2, Examples 14–17) in isooctane (30 g in Autoclave 1; 70 g in Autoclave 2) and continuous stirring was applied for 30 minutes. The reactor contents were discharged via a tap in the base of the autoclave.

The reactor was evacuated to 0.02 bar and loaded with the amounts of isooctane reported in Table 1; the reactor was heated to 50° C. and pressurized to 600 kPa with ethylene. The amounts of component (C) indicated in Table 1 (reactor) and n-hexylbenzene (0.5–3.5 g) as internal standard were added to the reactor and the stirring was continued for 30 minutes. A catalyst system prepared as described above, containing {1,2-Bis(t-butylamide)tetramethyldisilane}-zirconium dibenzyl (Component A) and [Me$_2$PhNH]$^+$[B (C$_6$F$_5$)$_4$]$^-$ (Component B) in the amounts reported in Table 1, was introduced into the reactor using an injection system. In autoclave 2, an additional amount of isooctane (about 4 g) was utilized in the injection of the catalyst solution. Addition of the catalyst solution resulted in a moderate exotherm (in the range of 51–57° C.), which reached a maximum within 1–2 minutes and was followed by rapid re-establishment of the original temperature. Temperature and pressure were monitored throughout the reaction, as well as ethylene consumption, whilst maintaining a constant ethylene pressure. After 60 minutes, the oligomerization was stopped by rapid venting of the ethylene, decanting the product mixture into a collection bottle using a tap in the base of the autoclave and opening of the autoclave. Exposure of the mixture to air resulted in rapid deactivation of the catalyst. All the reaction conditions are reported in Table 1.

The small amount of polyethylene (PE) by-product contained in the crude reaction product mixture was collected by filtration, followed by washing with hexane (500 ml) for 1 hour. The polymer was dried overnight (13 kpa, 70° C.) applying a stream of $N_2$ and finally weighed. The yields of oligomers and PE are reported in Table 2 and give a measure of the selectivity of the catalyst towards oligomerization compared to polymerization. The amount of the $C_6$ fraction in the final product is reported in Table 2 (Yld. Hexene); the composition of said $C_6$ fraction, made up of 1-hexene (1-H), cis-2-hexene (c-2-H), trans-2-hexene (t-2-H) and 2-ethyl-1-butene (2-ED), is reported in Table 3.

Furthermore, the amount of the $C_{12}$ fraction in the final product is reported in Table 2 (Yld. Dodecene); the composition of said $C_{12}$ fraction is reported in Table 3.

The obtained data demonstrate the unexpectedly higher oligomerization activities obtained with the catalyst systems according to the present invention, in comparison with the activities obtainable with the catalysts known in the state of the art, wherein no organometallic aluminium compounds are used (Comp. Example 1).

Furthermore, catalyst compositions containing organometallic aluminium compounds not envisaged by the specific class according to the present invention show poor oligomerization yields (see Comp. Examples 2, 4 and 13, in comparison with Examples 3, 9 and 14 respectively).

Finally, the obtained results sustain the inventiveness of the catalyst systems according to the present invention, wherein component (C) is selected among a specified group of compounds; in fact, Comp. Example 8 shows that a catalyst comprising MAO is able to exert only a poor activity in ethylene oligomerization, much lower than the activities shown by the organometallic aluminium compounds of the invention (see Examples 9–12).

TABLE 1

| Example | Reactor | Component (A) ($\mu$mol) | Component (B) ($\mu$mol) | Component (C) | (C) premix (mmol) | (C) reactor (mmol) | Toluene (g) | Isooctane (g) |
|---|---|---|---|---|---|---|---|---|
| COMP. 1 | 1 | 14.1 | 14.9 | none | 0 | 0 | 11.2 | 190 |
| COMP. 2 | 1 | 16.4 | 16.9 | TIBA | 0.37 | 0.87 | 11.2 | 190 |
| 3 | 1 | 14.4 | 15.3 | TIBAO | 0.37 | 0.88 | 11.2 | 190 |
| COMP. 4 | 1 | 7.3 | 7.8 | TIBA | 0.18 | 0.42 | 5.6 | 196 |
| 5 | 1 | 7.5 | 7.8 | TIOA | 0.19 | 0.41 | 5.6 | 196 |
| 6 | 1 | 7.4 | 7.7 | TDMBA | 0.19 | 0.42 | 5.6 | 196 |
| 7 | 1 | 7.4 | 7.8 | TDMHA | 0.17 | 0.45 | 5.6 | 196 |
| COMP. 8 | 1 | 7.5 | 7.8 | MAO | 0.18 | 0.45 | 5.5 | 196 |
| 9 | 1 | 7.3 | 7.5 | TIBAO | 0.21 | 0.45 | 5.6 | 196 |
| 10 | 1 | 7.4 | 8.2 | TIOAO | 0.23 | 0.49 | 5.6 | 196 |
| 11 | 1 | 7.3 | 7.3 | TDMBAO | 0.18 | 0.45 | 5.6 | 196 |
| 12 | 1 | 7.7 | 7.9 | TDMHAO | 0.19 | 0.42 | 5.6 | 196 |
| COMP. 13 | 2 | 14.8 | 15.3 | TIBA | 0.37 | 0.90 | 11.3 | 207 |
| 14 | 2 | 15.3 | 15.5 | TIBAO | 0.38 | 1.02 | 11.3 | 229 |
| 15 | 2 | 15.4 | 17.9 | TIBAO | 0.01 | 0.72 | 11.3 | 228 |
| 16 | 2 | 14.9 | 14.7 | TIBAO | 0.19 | 0.50 | 11.3 | 228 |
| 17 | 2 | 15.3 | 16.4 | TIBAO | 0.10 | 0.26 | 11.3 | 228 |

TABLE 2

| Example | Comp. (C) | Yld. $C_4$–$C_{30}$ α-olefins (g) | Activity $C_4$–$C_{30}$ α-olefins (Kg/gZr.h) | Yld. PE (g) | Yld. PE (% wt.) | Yld. Hexene (g) | Yld. Dodecene (g) | K factor |
|---|---|---|---|---|---|---|---|---|
| COMP. 1 | none | 38.9 | 30.3 | 0.3 | 0.7 | 5.7 | 5.3 | 0.72 |
| COMP. 2 | TIBA | 80.2 | 53.4 | 1.4 | 1.7 | 10.7 | 10.2 | 0.73 |
| 3 | TIBAO | 99.0 | 75.1 | 0.4 | 0.4 | 14.8 | 12.5 | 0.72 |
| COMP. 4 | TIBA | 28.5 | 43.0 | 0.4 | 1.4 | 4.0 | 3.8 | 0.73 |
| 5 | TIOA | 58.3 | 85.0 | 0.9 | 1.5 | 8.6 | 7.5 | 0.71 |
| 6 | TDMBA | 56.0 | 83.2 | 1.6 | 2.8 | 7.7 | 7.1 | 0.73 |
| 7 | TDMHA | 61.0 | 90.0 | 1.0 | 1.7 | 8.4 | 7.9 | 0.73 |
| COMP. 8 | MAO | 26.6 | 38.7 | 0.35 | 1.3 | 4.0 | 3.5 | 0.72 |
| 9 | TIBAO | 64.7 | 97.7 | 1.3 | 1.9 | 9.8 | 8.8 | 0.70 |
| 10 | TIOAO | 71.7 | 105.8 | 4.8 | 6.3 | 9.6 | 9.3 | 0.73 |
| 11 | TDMBAO | 73.6 | 109.9 | 2.0 | 2.6 | 11.7 | 10.1 | 0.69 |
| 12 | TDMHAO | 77.7 | 110.8 | 1.2 | 1.6 | 11.7 | 10.5 | 0.70 |
| COMP. 13 | TIBA | 67.6 | 50.1 | 0.3 | 0.4 | 10.6 | 8.0 | 0.67 |
| 14 | TIBAO | 106.7 | 76.3 | 0.3 | 0.3 | 18.9 | 12.6 | 0.68 |
| 15 | TIBAO | 151.3 | 107.7 | 0.1 | 0.1 | 26.5 | 17.9 | 0.68 |
| 16 | TIBAO | 116.8 | 85.9 | 0.4 | 0.3 | 22.4 | 13.2 | 0.69 |
| 17 | TIBAO | 128.5 | 92.4 | 0.4 | 0.3 | 24.9 | 14.6 | 0.68 |

TABLE 3

| Example | Comp. (C) | Yld. Hexene (g) | 1-H* (% wt.) | c-2-H* (% wt.) | t-2-H* (% wt.) | 2-EB* (% wt.) | Yld. Dodecene (g) | 1-Dodecene (% wt.) |
|---|---|---|---|---|---|---|---|---|
| COMP. 1 | none | 5.7 | 99.84 | 0.05 | 0.03 | 0.07 | 5.3 | 99.0 |
| COMP. 2 | TIBA | 10.7 | 99.53 | 0.07 | 0.00 | 0.40 | 10.2 | 96.9 |
| 3 | TIBAO | 14.8 | 99.46 | 0.10 | 0.07 | 0.37 | 12.5 | 97.4 |
| COMP. 4 | TIBA | 4.0 | 99.67 | 0.00 | 0.00 | 0.33 | 3.8 | 98.1 |
| 5 | TIOA | 8.6 | 99.73 | 0.05 | 0.00 | 0.22 | 7.5 | 98.2 |
| 6 | TDMBA | 7.7 | 99.66 | 0.0 | 0.00 | 0.27 | 7.1 | 97.8 |
| 7 | TDMHA | 8.4 | 99.72 | 0.06 | 0.00 | 0.21 | 7.9 | 97.5 |
| COMP. 8 | MAO | 4.0 | 99.73 | 0.05 | 0.00 | 0.22 | 3.5 | 98.4 |
| 9 | TIBAO | 9.8 | 99.68 | 0.10 | 0.00 | 0.22 | 8.8 | 97.9 |
| 10 | TIOAO | 9.6 | 99.70 | 0.07 | 0.00 | 0.23 | 9.3 | 97.8 |
| 11 | TDMBAO | 11.7 | 99.67 | 0.07 | 0.06 | 0.20 | 10.1 | 97.6 |
| 12 | TDMHAO | 11.7 | 99.67 | 0.10 | 0.00 | 0.17 | 10.5 | 97.6 |
| COMP. 13 | TIBA | 10.6 | 99.53 | 0.08 | 0.00 | 0.39 | 8.0 | 97.3 |
| 14 | TIBAO | 18.9 | 99.56 | 0.09 | 0.08 | 0.27 | 12.6 | 97.9 |
| 15 | TIBAO | 26.5 | 99.49 | 0.13 | 0.10 | 0.28 | 17.9 | 97.3 |
| 16 | TIBAO | 22.4 | 99.56 | 0.08 | 0.12 | 0.24 | 13.2 | 96.9 |
| 17 | TIBAO | 24.9 | 99.67 | 0.05 | 0.08 | 0.19 | 14.6 | 97.1 |

*1-H = 1-hexene;
c-2-H = cis-2-hexene;
t-2-H = trans-2-hexene;
2-EB = 2-ethyl-1-butene

What is claimed is:

1. A catalyst system for α-olefin oligomerization comprising the product obtainable by contacting the following components:

(A) one or more bis-amido compounds having formula (I):

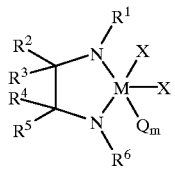

(I)

wherein M is Ti, Zr or Hf;

N is a trivalent nitrogen atom;

the Y atoms, the same or different from each other, are selected from the group consisting of Si, Ge and Sn;

the X groups, the same or different from each other, are selected from the group consisting of hydrogen, halogen, linear or branched, saturated or unsaturated $C_1-C_{20}$ alkyl, $C_1-C_{20}$ alkoxyl, $C_3-C_{20}$ cycloalkyl, $C_6-C_{20}$ aryl, $C_6-C_{20}$ aryloxyl, $C_7-C_{20}$ alkylaryl and $C_7-C_{20}$ arylalkyl radicals, optionally containing one or more Si, Ge, O, S, P, B or N atoms; or two X groups form a ring having from 4 to 8 members;

$R^1$, $R^2$, $R^3$, $R^4$, $R^5$ and $R^6$, the same or different from each other, are linear or branched, saturated or unsaturated $C_1-C_{20}$ alkyl, $C_3-C_{20}$ cycloalkyl, $C_6-C_{20}$ aryl, $C_7-C_{20}$ alkylaryl or $C_7-C_{20}$ arylalkyl radicals, optionally containing one or more Si, Ge, O, S, P, B or N atoms; or are $Si(R^7)_3$ groups, wherein the groups $R^7$, the same or different from each other, are linear or branched, saturated or unsaturated $C_1-C_{10}$ alkyl, $C_3-C_{10}$ cycloalkyl, $C_6-C_{15}$ aryl, $C_7-C_{15}$ alkylaryl or $C_7-C_{15}$ arylalkyl groups; or two or four substituents of $R^1$, $R^2$, $R^3$, $R^4$, $R^5$ and $R^6$, linked to two vicinal atoms, form one or two rings having from 4 to 8 members;

Q is a neutral Lewis base; and m is an integer ranging from 0 to 2;

said bis-amido compound being optionally present in the form of a dimer;

(B) one or more activating cocatalysts selected from:
compounds having formula $Y^+Z^-$, wherein $Y^+$ is a cation capable of reacting irreversibly with a substituent X of the compound of formula (I), and $Z^-$ is a compatible non-coordinating anion comprising at least one boron atom; and
neutral strongly Lewis acidic compounds comprising at least one boron atom;

(C) one or more compounds selected from the following classes:

(a) organometallic aluminum compounds having formula (II):

$Al(CH_2-CR^8R^9R^{10})_xR^{11}_yH_z$ (II)

wherein, in the $(CH_2-CR^8R^9R^{10})$ groups, the same or different from each other, $R^8$ is a linear or branched, saturated or unsaturated $C_1-C_{10}$ alkyl, $C_3-C_{13}$ cycloalkyl or $C_7-C_{16}$ alkylaryl radical;
$R^9$ is a saturated or unsaturated $C_1-C_{50}$ alkyl, $C_3-C_{50}$ cycloalkyl, $C_6-C_{50}$ aryl, $C_7-C_{50}$ alkylaryl or $C_7-C_{50}$ arylalkyl radical, said radical being different from a straight alkyl or alkenyl group;
or $R^8$ and $R^9$ form together a ring having from 4 to 6 carbon atoms;
$R^{10}$ is hydrogen or a linear or branched, saturated or unsaturated $C_1-C_{10}$ alkyl, $C_6-C_{15}$ aryl, $C_7-C_{16}$ alkylaryl radical or arylalkyl radical, optionally containing one or more Si or Ge atoms;
$R^{11}$ is a linear or branched, saturated or unsaturated $C_1-C_{15}$ alkyl, $C_3-C_{15}$ cycloalkyl, $C_6-C_{15}$ aryl, $C_7-C_{16}$ alkylaryl or $C_7-C_{16}$ arylalkyl radical; x is an integer ranging from 1 to 3; z is 0 or 1; and y is 3-x-z; and (b) the reaction products of water with organometallic aluminum compounds of formula (III):

$AlR^{12}_{3-w}H_w$ (III)

wherein the substituents $R^{12}$, the same or different from each other, are selected from the group consisting of linear or branched, saturated or unsaturated $C_1$–$C_{50}$ alkyl, $C_3$–$C_{50}$ cycloalkyl, $C_6$–$C_{50}$ aryl, $C_7$–$C_{50}$ alkylaryl and $C_7$–$C_{50}$ arylalkyl radicals, optionally containing one or more Si or Ge atoms, wherein at least one of said substituents $R^{12}$ is different from a straight alkyl group; and w is 0 or 1; the molar ratio between said organometallic aluminum compound and water being comprised between 1:1 and 100:1.

2. The catalyst system according to claim 1 wherein said bis-amido compound is present in the form of a dimer having formula (IV):

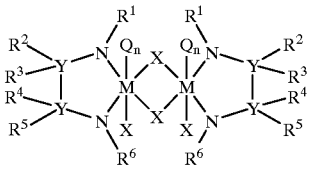

(IV)

wherein M, Y, X, $R^1$, $R^2$, $R^3$, $R^4$, $R^5$, $R^6$ and Q have the meaning reported in claim 1, and n is 0 or 1.

3. The catalyst system according to claim 1 wherein said bis-amido compound of formula (I) or (IV), M is Zr and the Y atoms are Si atoms.

4. The catalyst system according to claim 1 wherein said bis-amido compound of formula (I) or (IV), X is selected from the group consisting of hydrogen, methyl, ethyl, propyl, n-butyl, phenyl, 4-alkyl-phenyl and benzyl radicals.

5. The catalyst system according to claim 1 wherein said bis-amido compound of formula (I) or (IV), $R^1$, $R^2$, $R^3$, $R^4$, $R^5$ and $R^6$ are selected from the group consisting of methyl, ethyl, propyl, n-butyl, t-butyl, t-amyl, 1,1,3,3-tetramethylbutyl, cyclohexyl, phenyl, dimethyl-phenyl, diisopropyl-mehtyl, trimethyl-silyl, tri-t-butyl-silyl phenylmethyl-ethyl, diphenyl-ethyl and triphenyl-methyl.

6. The catalyst system according to claim 1 wherein said bis-amido compound of formula (I) OR (IV), Q is selected from the group consisting of diethylether, tetrahydrofuran, dimethylaniline, aniline, n-butylamine and trimethylphosphine.

7. The catalyst system according to claim 1 wherein said activating cocatalyst of formula $Y^+Z^-$, $Y^+$ is a quaternary ammonium cation or a metal cation, and $Z^-$ is a borate of formula $[B(R^1)_4]^-$, wherein $R^1$ is selected from the group consisting of hydrogen, $C_1$–$C_{10}$ alkyl, C3–$C_{10}$ cycloalkyl, $C_6$–$C_{15}$ aryl, $C_7$–$C_{15}$ alkylaryl and $C_7$–$C_{15}$ arylalkyl groups, optionally substituted with one or more halogens.

8. The catalyst system according to claim 7 wherein $Y^+$ is tri-n-butylammonium or dimethylanilinium, and $Z^-$ is selected from the group consisting of $[B(C_6F_5)_4]^-$, $[R^1B(C_6F_5)_3]^-$, $[B(FC_6H_4)_4]^-$, $[R^1B(FC_6H_4)_3]^-$, $[\{(CF_3)_2(C_6H_3)\}_4]^-$ and $[R^1B\{(CF_3)_2(C_6H_3)\}_3]^-$, wherein $R^1$ has the meaning reported in claim 7.

9. The catalyst system according to claim 1 wherein said activating cocatalyst is a neutral strongly Lewis acidic compound selected from tris(pentafluorophenyl)borane, tris (2,3,5,6-tetrafluorophenyl)borane and trimethylboron.

10. The catalyst system according to claim 1 wherein said organometallic aluminum compound of formula (II), $R^8$ is methyl or ethyl; $R^9$ is a branched $C_4$–$C_{10}$ alkyl or alkylaryl group, or a phenyl group; $R^{10}$ is hydrogen; and $R^{11}$ is a $C_1$–$C_5$ alkyl group.

11. The catalyst system according to claim 1 wherein said organometallic aluminum compound of formula (II), the ($CH_2$—$CR^8R^9R^{10}$) groups, the same or different from each other, are β,δ-branched groups.

12. The catalyst system according to claim 11 wherein said organometallic aluminum compound of formula (II) is selected from the group consisting of tris(2,4,4-trimethylpentyl)aluminum, bis(2,4,4-trimethylpentyl) aluminum hydride, isobutyl-bis(2,4,4-trimethylpentyl) aluminum, diisobutyl-(2,4,4-trimethylpentyl)aluminum, tris (2,4-dimethylheptyl)aluminum and bis(2,4-dimethylheptyl) aluminum hydride.

13. The catalyst system according to claim 11 wherein said β,δ-branched groups correspond to formula ($CH_2$—$CR^8R^{10}$—$CH_2$—$CR^{13}R^{14}R^{15}$), wherein $R^8$ and $R^{10}$ have the meaning reported in claim 1; $R^{13}$ and $R^{14}$, the same or different from each other, are linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals; and $R^{15}$ is hydrogen or has the same meaning of $R^{13}$ and $R^{14}$.

14. The catalyst system according to claim 1 wherein said organometallic aluminum compound of formula (II), the ($CH_2$—$CR^8R^9R^{10}$) groups, the same or different from each other, are β,γ-branched groups.

15. The catalyst system according to claim 14 wherein said β,γ-branched groups correspond to formula ($CH_2$—$CR^8R^{10}$—$CR^{13}R^{14}R^{15}$), wherein $R^8$ and $R^{10}$ have the meaning reported in claim 1; $R^{13}$ and $R^{14}$, the same or different from each other, are linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radicals; and $R^{15}$ is hydrogen or has the same meaning of $R^{13}$ and $R^{14}$.

16. The catalyst system according to claim 15 wherein said organometallic aluminum compound of formula (II) is selected from the group consisting of:
tris(2,3-dimethyl-butyl)aluminum, tris(2,3,3-trimethyl-butyl)aluminum, tris(2,3-dimethyl-pentyl)aluminum, tris(2,3-dimethyl-hexyl)aluminum, tris(2,3-dimethyl-heptyl)aluminum, tris(2-methyl-3-ethyl-pentyl) aluminum, tris(2-methyl-3-ethyl-hexyl)aluminum, tris (2-methyl-3-ethyl-heptyl)aluminum, tris(2-methyl-3-propyl-hexyl)aluminum, tris(2-ethyl-3-methyl-butyl) aluminum, tris(2-ethyl-3-methyl-pentyl)aluminum, tris (2,3-diethyl-pentyl)aluminum, tris(2-propyl-3-methyl-butyl)aluminum, tris(2-isopropyl-3-methyl-butyl) aluminum, tris(2-isobutyl-3-methyl-pentyl)aluminum, tris(2,3,3-trimethyl-pentyl)aluminum, tris(2,3,3-trimethyl-hexyl)aluminum, tris(2-ethyl-3,3-dimethyl-butyl)aluminum, tris(2-ethyl-3,3-dimethyl-pentyl) aluminum, tris(2-isopropyl-3,3-dimethyl-butyl) aluminum, tris(2-trimethylsilyl-propyl)aluminum, tris (2-methyl-3-phenyl-butyl)aluminum, tris(2-ethyl-3-phenyl-butyl)aluminum and tris(2,3-dimethyl-3-phenyl-butyl)aluminum.

17. The catalyst system according to claim 1 wherein said organometallic aluminum compound of formula (III), $R^{12}$ is a substituted or unsubstituted non-straight $C_1$–$C$ alkyl or $C_7$–$C_{16}$ alkylaryl, optionally containing Si or Ge atoms.

18. The catalyst system according to claim 17 wherein said organometallic aluminum compound of formula (III) is selected from the group consisting of $Al(iBu)_3$, $AlH(iBu)_2$, $Al(iHex)_3$, $Al(C_6H_5)_3$, $Al(CH_2C_6H_5)_3$, $Al(CH_2CMe_3)_3$, $Al(CH_2SiMe_3)_3$, $AlMe_2iBu$ and $AlMe(iBu)_2$.

19. The catalyst system according to claim 17 wherein said organometallic aluminum compound of formula (III), at least one group $R^{12}$ is a β,γ-branched group.

20. The catalyst system according to claim 19 wherein said organometallic aluminum compound is tris(2,3-dimethyl-butyl)aluminum or tris(2,3-dimethyl-hexyl) aluminum.

21. The catalyst system according to claim 17 wherein said organometallic aluminum compound of formula (III), at least one group $R^{12}$ is a β,δ-branched group.

22. The catalyst system according to claim 21 wherein said organometallic aluminum compound is tris(2,4,4-trimethylpentyl)aluminum.

23. The catalyst system according to claim 1 wherein, in component C, the molar ratio between said organometallic aluminum compound of formula (III) and water ranges from 1:1 to 50:1.

24. The catalyst system according to claim 1 wherein the molar ratio between component (A) and component (B) ranges from 0.1:1 to 5:1.

25. The catalyst system according to claim 1 wherein the molar ratio between the aluminum of component (C) and the metal M of the component (A) ranges from 10:1 to 500:1.

26. The catalyst system according to claim 1 wherein component (C) comprises organometallic aluminum compounds having formula (II):

wherein, in the $(CH_2-CR^8R^9R^{10})$ groups, the same or different from each other, $R^8$ is a linear or branched, saturated or unsaturated $C_1-C$ alkyl, $C_3-C_{13}$ cycloalkyl or $C_7-C16$ alkylaryl radical;

$R^9$ is a saturated or unsaturated $C_1-C_{50}$ alkyl, $C_3-C_{50}$ cycloalkyl, $C_6-C_{50}$ aryl, $C_7-C_{50}$ alkylaryl or $C_7-C_{50}$ arylalkyl radical, said radical being different from a straight alkyl or alkenyl group;

or $R^8$ and $R^9$ form together a ring having from 4 to 6 carbon atoms;

$R^{10}$ is hydrogen or a linear or branched, saturated or unsaturated $C_1-C$ alkyl, $C_6-C_{15}$ aryl, $C_7-C_{16}$ alkylaryl radical or arylalkyl radical, optionally containing one or more Si or Ge atoms;

$R^{11}$ is a linear or branched, saturated or unsaturated $C_1-C$ alkyl, $C_3-C_{15}$ cycloalkyl, $C_6-C_{15}$ aryl, $C_7-C_{16}$ alkylaryl or $C_7-C_{16}$ arylalkyl radical; and x is an integer ranging from 1 to 3; z is 0 or 1; and y is 3-x-z.

27. The catalyst system according to claim 1 wherein component (C) comprises the the reaction products of water with organometallic aluminum compounds of formula (III):

wherein the substituents $R^{12}$, the same or different from each other, are selected from the group consisting of linear or branched, saturated or unsaturated $C_1-C_{50}$ alkyl, $C_3-C_{50}$ cycloalkyl, $C_6-C_{50}$ aryl, $C_7-C_{50}$ alkylaryl and $C_7-C_{50}$ arylalkyl radicals, optionally containing one or more Si or Ge atoms, wherein at least one of said substituents $R^{12}$ is different from a straight alkyl group; and w is 0 or 1; the molar ratio between said organometallic aluminum compound and water being comprised between 1:1 and 100:1.

28. The catalyst system according to claim 26 wherein said organometallic aluminum compound of formula (II) is selected from the group consisting of tris(2,4,4-trimethylpentyl)aluminum, bis(2,4,4-trimethylpentyl) aluminum hydride, isobutyl-bis(2,4,4-trimethylpentyl) aluminum, diisobutyl-(2,4,4-trimethylpentyl)aluminum, tris(2,4-dimethylheptyl)aluminum and bis(2,4-dimethylheptyl) aluminum hydride, tris(2,3-dimethyl-butyl)aluminum, tris(2,3,3-trimethyl-butyl)aluminum, tris(2,3-dimethyl-pentyl) aluminum, tris(2,3-dimethyl-hexyl)aluminum, tris(2,3-dimethyl-heptyl)aluminum, tris(2-methyl-3-ethyl-pentyl) aluminum, tris(2-methyl-3-ethyl-hexyl)aluminum, tris(2-methyl-3-ethyl- heptyl)aluminum, tris(2-methyl-3-propyl-hexyl)aluminum, tris(2-ethyl-3-methyl-butyl)aluminum, tris(2-ethyl-3-methyl-pentyl)aluminum, tris(2,3-diethyl-pentyl) aluminum, tris(2-propyl-3-methyl-butyl)aluminum, tris(2-isopropyl-3-methyl-butyl)aluminum, tris(2-isobutyl-3-methyl-pentyl)aluminum, tris(2,3,3-trimethyl-pentyl) aluminum, tris(2,3,3-trimethyl-hexyl)aluminum, tris(2-ethyl-3,3-dimethyl-butyl)aluminum, tris(2-ethyl-3,3-dimethyl-pentyl)aluminum, tris(2-isopropyl-3,3-dimethyl-butyl)aluminum, tris(2-trimethylsilyl-propyl)aluminum, tris (2-methyl-3-phenyl-butyl)aluminum, tris(2-ethyl-3-phenyl-butyl)aluminum and tris(2,3-dimethyl-3-phenyl-butyl) aluminum.

29. The catalyst system according to claim 27 wherein said organometallic aluminum compound of formula (III) is selected from the group consisting of $Al(iBu)_3$, $AlH(iBu)_2$, $Al(iHex)_3$, $Al(C_6H_5)_3$, $Al(CH_2C_6H_5)_3$, $Al(CH_2CMe_3)_3$, $Al(CH_2SiMe_3)_3$, $AlMe_2iBu$, $AlMe(iBu)_2$, tris(2,3-dimethyl-butyl)aluminum, tris(2,3-dimethyl-hexyl)aluminum, and tris (2,4,4-trimethylpentyl)aluminum.

30. The catalyst system according to claim 26 wherein said organometallic aluminum compound of formula (II), the $(CH_2-CR^8R^9R^{10})$ groups, the same or different from each other, are β,δ-branched groups.

31. The catalyst system according to claim 30 wherein said orgarometallic aluminum compound of formula (II) is selected from the group consisting of tris(2,4,4-trimethylpentyl)aluminum, bis(2,4,4-trimethylpentyl) aluminum hydride, isobutyl-bis(2,4,4-trimethylpentyl) aluminum, diisobutyl-(2,4,4-trimethylpentyl)aluminum, tris (2,4-dimethylheptyl)aluminum and bis(2,4-dimethylheptyl) aluminum hydride.

32. The catalyst system according to claim 30 wherein said β,δ-branched groups correspond to formula $(CH_2-CR^8R^{10}-CH_2-CR^{13}R^{14}R^{15})$, wherein $R^8$ and $R^{10}$ have the meaning reported in claim 1; $R^{13}$ and $R^{14}$, the same or different from each other, are linear or branched, saturated or unsaturated $C_1-C_{20}$ alkyl, $C_3-C_{20}$ cycloalkyl, $C_6-C_{20}$ aryl, $C_7-C_{20}$ alkylaryl and $C_7-C_{20}$ arylalkyl radicals; and $R^{15}$ is hydrogen or has the same meaning of $R^{13}$ and $R^{14}$.

33. The catalyst system according to claim 26 wherein said organometallic aluminum compound of formula (II), the $(CH_2-CR^8R^9R^{10})$ groups, the same or different from each other, are β,γ-branched groups.

34. The catalyst system according to claim 33 wherein said β,γ-branched groups correspond to formula $(CH_2-CR^8R^{10}-CR^{13}R^{14}R^{15})$, wherein $R^8$ and $R^{10}$ have the meaning reported in claim 1; $R^{13}$ and $R^{14}$, the same or different from each other, are linear or branched, saturated or unsaturated $C_1-C_{20}$ alkyl, $C_3-C_{20}$ cycloalkyl, $C_6-C_{20}$ aryl, $C_7-C_{20}$ alkylaryl or $C_7-C_{20}$ arylalkyl radicals; and $R^{15}$ is hydrogen or has the same meaning of $R^{13}$ and $R^{14}$.

35. The catalyst system according to claim 34 wherein said organometallic aluminum compound of formula (II) is selected from the group consisting of:

tris(2,3-dimethyl-butyl)aluminum, tris(2,3,3-trimethyl-butyl)aluminum, tris(2,3-dimethyl-pentyl)aluminum, tris(2,3-dimethyl-hexyl)aluminum, tris(2,3-dimethyl-heptyl)aluminum, tris(2-methyl-3-ethyl-pentyl) aluminum, tris(2-methyl-3-ethyl-hexyl)aluminum, tris (2-methyl-3-ethyl-heptyl)aluminum, tris(2-methyl-3-propyl-hexyl)aluminum, tris(2-ethyl-3-methyl-butyl) aluminum, tris(2-ethyl-3-methyl-pentyl)aluminum, tris (2,3-diethyl-pentyl)alumina, tris(2-propyl-3-methyl-butyl)aluminum, tris(2-isopropyl-3-methyl-butyl) aluminum, tris(2-isobutyl-3-methyl-pentyl)aluminum, tris(2,3,3-trimethyl-pentyl)aluminum, tris(2,3,3-trimethyl-hexyl)aluminum, tris(2-ethyl-3,3-dimethyl-butyl)aluminum, tris(2-ethyl-3,3-dimethyl-pentyl) aluminum, tris(2-isopropyl-3,3-dimethyl-butyl)

aluminum, tris(2-trimethylsilyl-propyl)aluminum, tris(2-methyl-3-phenyl-butyl)aluminum, tris(2-ethyl-3-phenyl-butyl)aluminum and tris(2,3-dimethyl-3-phenyl-butyl)aluminum.

36. The catalyst system according to claim 27 wherein said organometallic aluminum compound of formula (III), $R^{12}$ is a substituted or unsubstituted non-straight $C_1$–C alkyl or $C_7$–$C_{16}$ alkylaryl, optionally containing Si or Ge atoms.

37. The catalyst system according to claim 36 wherein said organometallic aluminum compound of formula (III) is selected from the group consisting of $Al(iBu)_3$, $AlH(iBu)_2$, $Al(iHex)_3$, $Al(C_6H_5)_3$, $Al(CH_2C_6H_5)_3$, $Al(CH_2CMe_3)_3$, $Al(CH_2SiMe_3)_3$, $AlMe_2iBu$ and $AlMe(iBu)_2$.

38. The catalyst system according to claim 38 wherein said organometallic aluminum compound of formula (III), at least one group $R^{12}$ is a β,γ-branched group.

39. The catalyst system according to claim 38 wherein said organometallic aluminum compound is tris(2,3-dimethyl-butyl)aluminum or tris(2,3-dimethyl-hexyl)aluminum.

40. The catalyst system according to claim 36 wherein said organometallic aluminum compound of formula (III), at least one group $R^{12}$ is a β,δ-branched group.

41. The catalyst system according to claim 40 wherein said organometallic aluminum compound is tris(2,4,4-trimethylpentyl)aluminum.

42. The catalyst system according to claim 27 wherein the molar ratio between said organometallic aluminum compound of formula III) and water ranges from 1:1 to 50:1.

* * * * *

UNITED STATES PATENT AND TRADEMARK OFFICE
CERTIFICATE OF CORRECTION

PATENT NO.    : 6,372,684 B1                                               Page 1 of 1
DATED         : April 16, 2002
INVENTOR(S)   : Andrew D. Horton, Bart Johan Ruisch, Klaas L. von Hebel and Henderikus Hyacinthus Deuling It is certified that error appears in the above-identified patent and that said Letters Patent is hereby corrected as shown below:

<u>Title page,</u>
Item [73], Assignee: please delete "Shell Oil Company, Houston, TX (US)" and in its place -- Shell Research Limited, London, UK. --

Signed and Sealed this

Ninth Day of July, 2002

*Attest:*

JAMES E. ROGAN
*Attesting Officer*    *Director of the United States Patent and Trademark Office*

UNITED STATES PATENT AND TRADEMARK OFFICE
CERTIFICATE OF CORRECTION

PATENT NO. : 6,372,684 B1
DATED : April 16, 2002
INVENTOR(S) : Andrew D. Horton et al.

It is certified that error appears in the above-identified patent and that said Letters Patent is hereby corrected as shown below:

Title page,
Item [57], ABSTRACT,
Please delete the structure shown as:

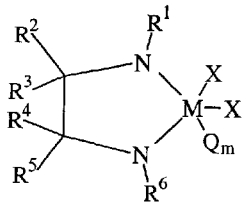

and insert in its place the following structure:

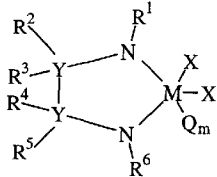

Column 1,
Lines 8 and 13, please delete the parenthesis "(" that appears before the word "α-olefins".

Column 2,
Line 15, please delete the open bracket "{" that appears after the word "disilane" and insert in its place a close bracket "}".

Column 3,
Line 5, please delete the structure shown as:

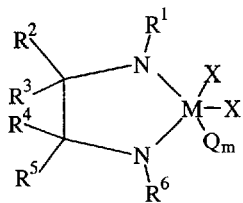

UNITED STATES PATENT AND TRADEMARK OFFICE
CERTIFICATE OF CORRECTION

PATENT NO.   : 6,372,684 B1
DATED        : April 16, 2002
INVENTOR(S)  : Andrew D. Horton et al.

It is certified that error appears in the above-identified patent and that said Letters Patent is hereby corrected as shown below:

Column 3 cont'd,
and insert in its place the following structure:

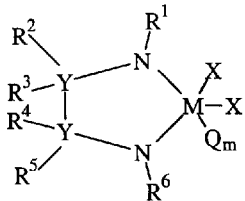

Line 42, please delete "Z-" and in its place insert -- Z⁻ --.
Line 57, please delete the comma "," after "$C_7$-$C_{50}$".

Column 5,
Line 22, please delete "ph" and insert in its place -- Ph --.
Line 53, please delete "Y⁻" and insert in its place -- $Y^+$ --.

Column 6,
Line 25, please delete "R6" and insert in its place -- $R^6$ --.
Line 37, please delete "$R^1$" and insert in its place -- $R^I$ --.

Column 7,
Line 21, please delete "(11)" and insert in its place -- (II) --.

Column 9,
Line 32, please delete "10.1" and insert in its place -- 10:1 --.
Line 53, please delete "a-olefins" and insert in its place -- α-olefins --.

Column 10,
Line 33, please insert a period -- . -- immediately after the word "reaction" before the word "The" within the text printed as "reaction The".

Column 11,
Line 28, please change the first letter in the word printed as "Dibenzyl" from an uppercase "D" to a lowercase "d".

UNITED STATES PATENT AND TRADEMARK OFFICE
CERTIFICATE OF CORRECTION

PATENT NO. : 6,372,684 B1
DATED : April 16, 2002
INVENTOR(S) : Andrew D. Horton et al.

It is certified that error appears in the above-identified patent and that said Letters Patent is hereby corrected as shown below:

Column 13,
Line 12, please delete "2-ED" and insert in its place -- 2-EB --.

Column 15,
Table 3, within the table column labeled "c-2-H*" at the table row labeled "6", please delete "0.0" and insert in its place -- 0.05 --.
Line 35, please delete the structure shown as:

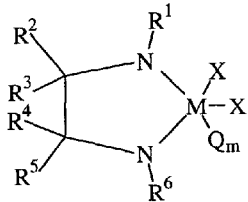

and insert in its place the following structure:

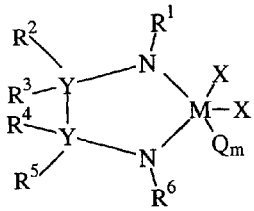

Column 16,
Line 57, please delete "$C_1$-C alkyl" and insert in its place -- $C_1$-$C_{10}$ alkyl --.

Column 17,
Line 46, please delete "C3-$C_{10}$" and insert in its place -- $C_3$-$C_{10}$ --.
Line 53, please delete "[{$(CF_3)_2(C_6H_3)$}$_4$]" and insert in its place
-- [B{$(CF_3)_2(C_6H_3)$}$_4$]$^-$ --.

UNITED STATES PATENT AND TRADEMARK OFFICE
CERTIFICATE OF CORRECTION

PATENT NO. : 6,372,684 B1
DATED : April 16, 2002
INVENTOR(S) : Andrew D. Horton et al.

It is certified that error appears in the above-identified patent and that said Letters Patent is hereby corrected as shown below:

Column 18,
Line 51, please delete "$C_1$-C alkyl" and insert in its place -- $C_1$-$C_{10}$ alkyl --.

Column 19,
Lines 22 and 36, please delete "$C_1$-C alkyl" and insert in its place -- $C_1$-$C_{10}$ alkyl --.
Line 23, please delete "$C_7$-C16" and insert in its place -- $C_7$-$C_{16}$ --.
Line 32, please delete "$C_1$-C alkyl" and insert in its place -- $C_1$-$C_{10}$ alkyl --.

Column 20,
Line 23, please delete "orgarometallic" and insert in its place -- organometallic --.
Line 61, please delete "alumina" and insert in its place -- aluminum --.

Column 21,
Line 8, please delete "$C_1$-C alkyl" and insert in its place -- $C_1$-$C_{10}$ alkyl --.
Line 15, please delete "according to claim 38" and in its place insert -- according to claim 36 --.

Column 22,
Line 15, please insert an open parenthesis -- ( -- before the numeral "III".

Signed and Sealed this

Sixteenth Day of December, 2003

JAMES E. ROGAN
*Director of the United States Patent and Trademark Office*